(12) United States Patent
Obenaus et al.

(10) Patent No.: US 7,304,188 B2
(45) Date of Patent: Dec. 4, 2007

(54) PREPARATION OF HIGHLY PURE METHYL TERT-BUTYL ETHER

(75) Inventors: Fritz Obenaus, Marl (DE); Wilhelm Droste, Marl (DE); Bernhard Scholz, Marl (DE); Franz Nierlich, Marl (DE); Rainer Malzkorn, Dorsten (DE); Udo Peters, Marl (DE); Jochen Praefke, Marl (DE); Richard Filipiak, Marl (DE); Joachim Neumeister, Haltern am See (DE)

(73) Assignee: OXENO Olefinchemie GmbH, Marl (DE)

( * ) Notice: Subject to any disclaimer, the term of this patent is extended or adjusted under 35 U.S.C. 154(b) by 11 days.

(21) Appl. No.: 10/519,397

(22) PCT Filed: Jun. 14, 2003

(86) PCT No.: PCT/EP03/06300

§ 371 (c)(1),
(2), (4) Date: Apr. 13, 2006

(87) PCT Pub. No.: WO2004/007412

PCT Pub. Date: Jan. 22, 2004

(65) Prior Publication Data

US 2006/0264681 A1    Nov. 23, 2006

(30) Foreign Application Priority Data

Jul. 10, 2002  (DE)  ................ 102 31 051

(51) Int. Cl.
C07C 41/58    (2006.01)
(52) U.S. Cl. .............. 568/699; 568/697; 585/639
(58) Field of Classification Search .......... None
See application file for complete search history.

(56) References Cited

U.S. PATENT DOCUMENTS

| 4,256,465 | A  | * | 3/1981  | Takezono et al. ............ 44/446 |
| 4,918,244 | A  | * | 4/1990  | Nelson et al. .............. 568/698 |
| 5,210,327 | A  |   | 5/1993  | Luebke et al. ............. 568/697 |
| 5,609,734 | A  |   | 3/1997  | Streicher et al. ........... 568/697 |
| 6,657,090 | B2 |   | 12/2003 | Rix et al. ................... 568/697 |
| 2004/0054246 | A1 | | 3/2004 | Nierlich et al. ............. 585/515 |
| 2004/0097773 | A1 | | 5/2004 | Beckmann et al. ......... 585/530 |
| 2006/0264681 | A1 | | 11/2006 | Obenaus et al. |

FOREIGN PATENT DOCUMENTS

EP    0 466 954    1/1992

OTHER PUBLICATIONS

U.S. Appl. No. 10/524,790, filed Feb. 16, 2005, Malzkorn et al.
U.S. Appl. No. 10/519,397, filed Jan. 3, 2005, Obenaus et al.
U.S. Appl. No. 10/543,148, filed Jul. 25, 2005, Peters et al.
U.S. Appl. No. 11/624,823, filed Jan. 19, 2007, Rix et al.
U.S. Appl. No. 11/521,460, filed Sep. 15, 2006, Rix et al.
U.S. Appl. No. 11/614,275, filed Dec. 21, 2006, Praefke et al.
U.S. Appl. No. 11/610,801, filed Dec. 14. 2006, Fernandez et al.

\* cited by examiner

*Primary Examiner*—Rosalynd Keys
(74) *Attorney, Agent, or Firm*—Oblon, Spivak, McClelland, Maier & Neustadt, P.C.

(57) ABSTRACT

The invention relates to a process for preparing methyl tert-butyl ether (MTBE) in qualities which are suitable for organic syntheses and for use as a specialty solvent from MTBE in fuel quality.

11 Claims, 3 Drawing Sheets

PREPARATION OF HIGHLY PURE METHYL TERT-BUTYL ETHER

CROSS REFERENCES TO RELATED APPLICATIONS

Figure 1:
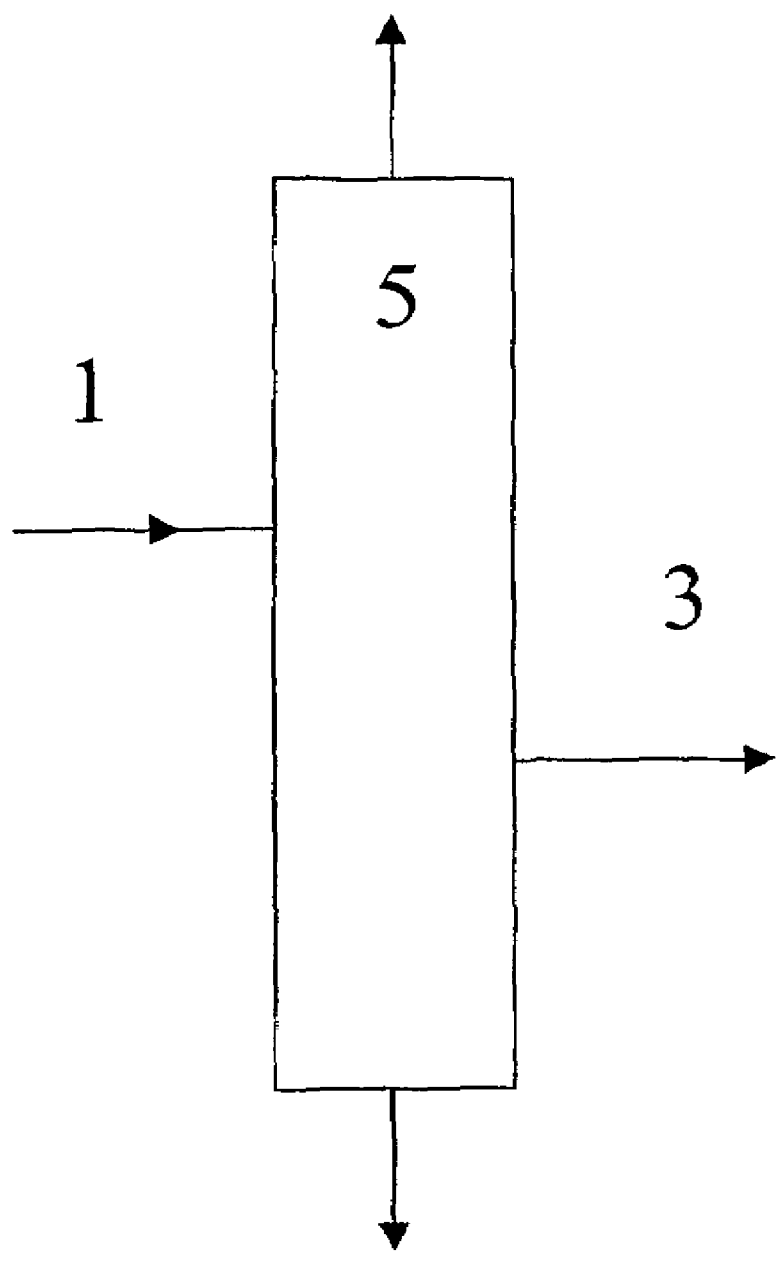

This application is a national stage application of International Patent Application No. PCT/EP03/06300, filed on Jun. 14, 2003, and claims priority to German Patent Application No. 102 31 051.3, filed on Jul. 10, 2002, both of which are incorporated herein by reference in their entireties.

The invention relates to a process for preparing methyl tert-butyl ether (MTBE) in qualities which are suitable for organic syntheses and for use as a specialty solvent from MTBE in fuel quality.

Technical grade MTBE is a sought-after component in fuels for gasoline engines to increase the octane number. With regard to purity, the demands made are none too high. The contents of methanol and tert-butanol may each be up to 1% by mass. Technical grade MTBE may also comprise up to 0.5% by mass of $C_4$-to $C_8$-hydrocarbons and up to 500 ppm of water (MTBE product information, Oxeno GmbH, March 2001).

The solvents and extractants used in the pharmaceuticals field and in analysis are highly pure solvents. When preparing organometallic compounds, for example Grignard compounds, and when reacting them, aprotic solvents having donor properties are used. To this end, the solvents used are frequently lower ethers, for example diethyl ether, diisopropyl ether, tetrahydrofuran or MTBE. The first three ethers mentioned have the disadvantage of a low ignition temperature and a wide explosion range. In the presence of oxygen, they also form peroxides extremely easily. Examples of accidents with peroxides, even resulting in death, are known from the relevant literature. In most applications, MTBE can be used instead of the first-named ethers. MTBE has the advantage that it forms no peroxides.

MTBE is obtained from isobutenic $C_4$ olefin mixtures, for example from the $C_4$ cut from steam crackers or FCC units. These mixtures consist substantially of butadiene, isobutene, 1-butene and the two 2-butenes, and also the saturated hydrocarbons isobutane and n-butane. Workup processes for such $C_4$ cuts which are practiced worldwide comprise the following steps: first, the majority of the butadiene is removed. When butadiene can be profitably marketed or there is an internal demand for it, it is removed, for example, by extraction or extractive distillation. Otherwise, it is selectively hydrogenated to linear butenes up to concentrations of from 1 to 0.1% by mass. In both cases, a hydrocarbon mixture (corresponding to raffinate I or hydrogenated crack-$C_4$) remains which, in addition to the saturated hydrocarbons (n-butane and isobutane), comprises the olefins (isobutene, 1-butene and 2-butenes). This hydrocarbon mixture is reacted with methanol in the presence of an acid catalyst, usually disposed in a fixed bed, which results in MTBE from the majority of the isobutene in accordance with the equilibrium position. The further workup of this reaction mixture is effected by distillation in a distillation column or in a reactive distillation column. The bottom product obtained in both cases is technical grade MTBE (fuel quality).

When the technical grade MTBE obtained in this way has to fulfill higher purity requirements, the impurities, mainly methanol and butanol, have to be removed.

The literature discloses several processes for removing methanol from MTBE streams. In some processes, the methanol is removed before or during the distillative separation of the MTBE synthesis reaction mixture. In other processes, the methanol is removed directly from the technical grade MTBE.

U.S. Pat. No. 3,726,942 describes an MTBE process in which methanol is removed by washing with water from the crude MTBE obtained by distillation after the synthesis. U.S. Pat. No. 3,846,088 discloses a process in which methanol is initially removed from the crude MTBE by extraction with water and then the water dissolved in the MTBE is removed by azeotropic distillation with $C_5$-$C_{10}$ paraffins.

U.S. Pat. No. 4,334,964 and U.S. Pat. No. 4,544,776 describe processes in which the methanol is washed out of the MTBE synthesis reaction mixture with water before the distillative separation.

U.S. Pat. No. 4,605,787 discloses an MTBE process in which methanol is removed from the crude MTBE obtained by distillation by adsorption on zeolitic molecular sieves (0.3 nm, 0.4 nm, 0.5 nm).

According to EP 0 317 918, methanol is removed with the aid of a membrane before or during the distillative MTBE removal.

According to DE 30 15 882, methanol is removed from crude MTBE by extractive distillation. The extractants used are one or more compounds from the groups of di-and trihydric alcohols, aminoalcohols and dimethyl-formamide.

According to U.S. Pat. No. 4,256,465, the methanol present in the crude MTBE is substantially removed by distilling off the MTBE/methanol azeotrope to obtain a highly pure MTBE stream. The azeotrope may be recycled into the MTBE synthesis reactor.

The abovementioned processes are lacking in that although they remove methanol and sometimes water from the crude MTBE, they do not remove other accompanying materials, for example $C_8$-olefins, tert-butanol (TBA) or 2-methoxybutane (MSBE). This can presumably be attributed to the fact that the separation in the existing distillation processes is carried out in such a way that MTBE is obtained as the bottom product (i.e. as the high boiler) and an azeotrope of methanol and MTBE or an azeotrope of $C_4$-hydrocarbons with methanol is obtained as the top product. This separation is unsuitable for preparing very pure MTBE, since MTBE and the oligomerization products of butenes (diisobutene) remain in the MTBE in excessive amounts.

It is therefore an object of the present invention to provide an inexpensive process for preparing highly pure methyl tert-butyl ether from technical grade MTBE (fuel quality of approx. 99% purity).

It has now been found that the desired purity of MTBE can be obtained by distillatively separating technical grade MTBE into three fractions, i.e. a low boiler fraction, a middle fraction and a high boiler fraction. The low boiler fraction comprises MTBE, methanol, water and also small amounts of $C_4$ and $C_5$ components. The middle fraction consists of MTBE in the desired purity. In addition to MTBE, the high boiler fraction comprises tert-butyl alcohol (TBA), olefins which have resulted from oligomerization of butenes, derivatives of these olefins and/or other by-products.

The present invention therefore provides a process for preparing MTBE having a purity of greater than 99.7% from technical grade MTBE by fractional distillation, by separating the technical grade MTBE into a low boiler fraction comprising MTBE, methanol and water, a middle fraction comprising MTBE in a purity of greater than 99.7% and a high boiler fraction comprising butene oligomers and TBA.

The process of the invention allows MTBE to be obtained in a purity of greater than 99.8% or 99.9%. The percentages always relate to % by mass. The technical grade MTBE used is customarily used as a fuel additive and has a maximum purity of 99.0%.

The fractional distillation may be carried out in one column, in particular at least two columns. Preference is given to using at least one dividing wall column.

The dividing wall column is a column which is separated into two parts by a vertical wall. This allows two distillation steps to be carried out in one apparatus, so that one column, and also one or two heat exchangers, may be dispensed with.

The process according to the invention has the following advantages:

The investment and operation costs are relatively low. The resulting low and high boiler fractions may be recycled without losses into a plant for preparing technical grade MTBE (fuel quality).

When the production ratio of highly pure MTBE to MTBE of fuel quality is low, both the low boiler and the high boiler fraction may be recycled into the fuel MTBE stream. When the ratios are larger, the low boiler fraction may be recycled into the MTBE synthesis, while the high boiler fraction may be utilized as a fuel component.

According to the invention, the removal of the highly pure MTBE is carried out in one or more distillation columns. Some possible embodiments are schematically illustrated in FIGS. 1-3.

Figure 2:
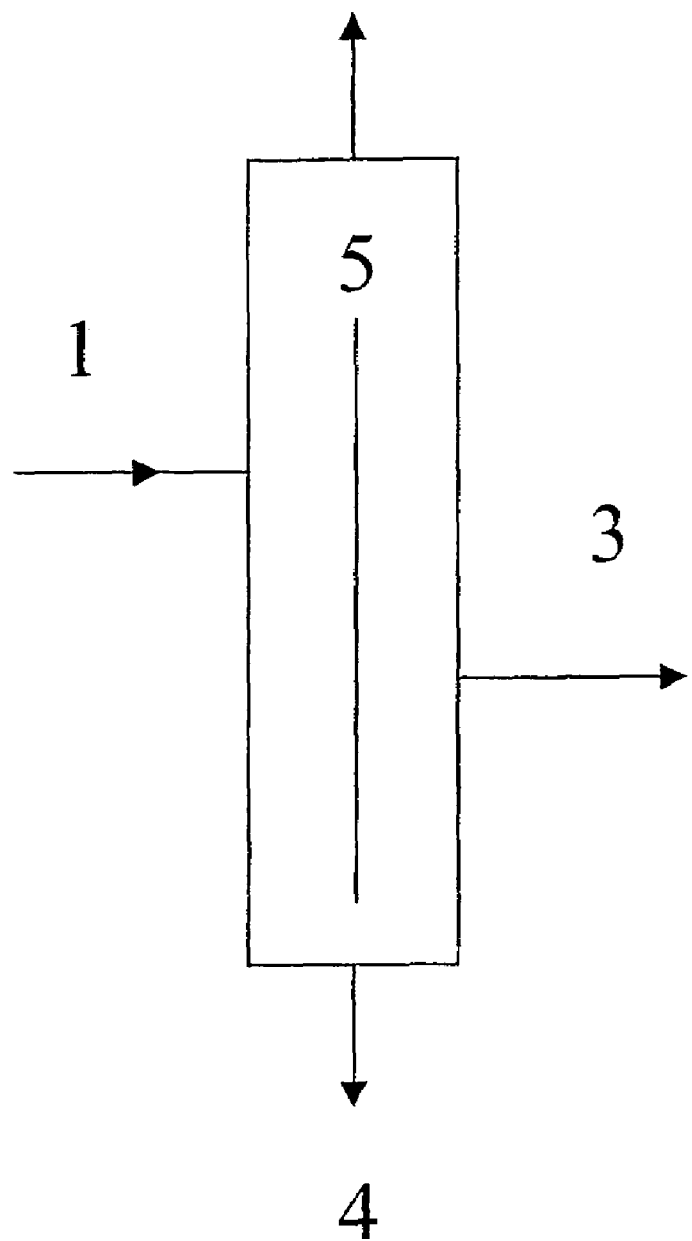

FIGS. 1 and 2 illustrate process variants in which highly pure MTBE is obtained in one column. The difference between these two variants is that a customary distillation column is used in the process of FIG. 1 and a dividing wall column is used in the process of FIG. 2. MTBE (technical grade quality) (1) is introduced into the distillation column (5). The top product (2) removed is a mixture of MTBE, methanol and water. The bottom product (4) obtained is a mixture of MTBE, tert-butyl alcohol (TBA), 2-methoxybutane (MSBE) and higher olefins. The highly pure MTBE (3) is withdrawn as a sidestream.

Figure 3:
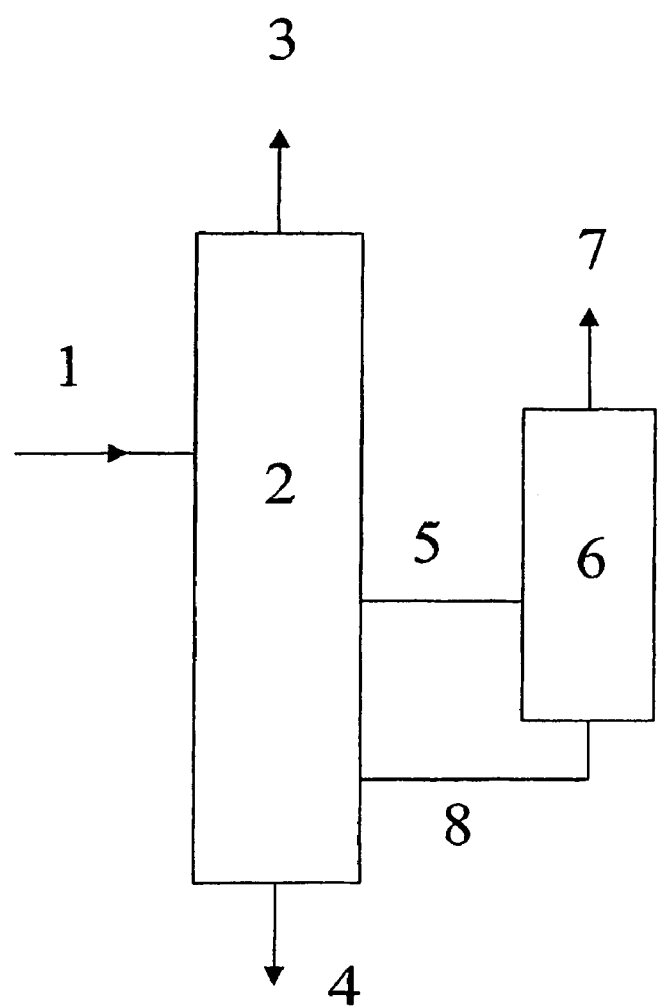

In the process variant of FIG. 3, MTBE in fuel quality (1) is introduced into the distillation column (2). Methanol and water together with a portion of the MTBE are removed as the top product (3) and high-boiling accompanying materials are removed with the bottoms (4). The sidestream (5) is separated in the side column (6) into highly pure MTBE (7) and a bottom product (8) which is recycled into the first column. (Depending on the procedure, the sidestream (5) may be removed from the secondary column (6) in liquid or vaporous form below or above the feed (1).)

In the process according to the invention, crude MTBE in fuel quality is worked up to give highly pure MTBE. Useful starting products are MTBE mixtures which may comprise, as accompanying materials, the low boilers methanol and water, and also the high boilers TBA, oligomers of $C_4$-olefins, the alcohols and methyl ethers derived therefrom and 2-methoxybutane (MSBE).

Preference is given to using crude MTBE in the process according to the invention which has been obtained by reacting raffinate I or hydrogenated crack-$C_4$ with methanol by known processes. This MTBE (fuel quality) typically has an MTBE content of from 98 to 99.0% by mass, a $C_8$-hydrocarbon content of less than 0.5% by mass, a TBA content of less than 1% by mass, a methanol content of less than 1% by mass and a water content of less than 0.05% by mass, and also a 2-methoxybutane (MSBE) content of up to 0.5% by mass.

The process according to the invention allows pure MTBE (purity greater than 99.7%) having a 2-methoxybutane content of less than 500 ppm by mass, in particular from 100 to 300 ppm by mass, to be obtained. To this end, it is advantageous, but not necessarily obligatory, to use MTBE in a quality having less than 0.3% by mass of 2-methoxybutane as the starting material. The preparation of MTBE (fuel quality) having a 2-methoxybutane content (MSBE) of less than 0.25% by mass is described, for example, in DE 101 02 082.1.

Optionally, crude MTBE mixtures which have been prepared in another way, for example from TBA and methanol, may also be used.

It is pointed out that the process according to the invention can also be used to work up crude MTBE mixtures whose compositions do not correspond to the above information in this or other respects to give highly pure MTBE.

Highly pure MTBE is obtained distillatively in one or more columns having internals which comprise trays, rotating trays, random and/or structured packings.

Useful column trays include the following types:

Trays having drillholes or slots in the tray plate.

Trays having throats or chimneys which are covered by bubble-caps, caps or hoods.

Trays having drillholes in the tray plate which are covered by movable valves.

Trays having special constructions.

In columns having rotating internals, the reflux is either sprayed by rotating funnels or distributed as a film onto a heated tube wall with the aid of a rotor.

Columns used in the process according to the invention may comprise random packings of various shaped bodies.

They may consist of almost any materials (steel, stainless steel, copper, carbon, stoneware, porcelain, glass, plastics, etc.) and in various shapes (spheres, rings having flat or profiled surfaces, rings having internal webs or wall breaches, wire mesh rings, saddles and spirals).

Structured packings having regular geometry may consist, for example, of sheets or weaves. Examples of such structured packings include Sulzer BX woven packings made of metal or plastic, Sulzer Mellapack lamella packings made of sheet metal, structured packings from Sulzer (Optiflow), Montz (BSH) and Kuhni (Rombopack).

The process according to the invention can be carried out at reduced, atmospheric or elevated pressure. A preferred pressure range is 1.5-10 bar, in particular 2-6 bar.

The low boiler fraction which consists substantially of an MTBE/methanol azeotrope is removed at a top temperature which is between the boiling point of the MTBE/methanol azeotrope and the boiling point of MTBE at the distillation pressure.

The high boiler fraction which consists mainly of MTBE and TBA is removed at a temperature which is between the boiling point of the MTBE and the boiling point of the TBA at the distillation pressure.

In a special embodiment of the invention, the fractional distillation is carried out in a two-column system which consists of a main column and a side column, and the low boiler fraction is obtained as the top product and the high boiler fraction as the bottom product of the main column and the middle fraction is purified in the side column to give the desired MTBE having a purity of 99.7%.

Depending on the procedure, the MTBE having a purity of greater than 99.7% may be obtained as the top or bottom product of the side column. The other fractions in each case which do not contain the desired MTBE may optionally be recycled into the main column. One of these variants is outlined in FIG. 3.

When the sidestream takeoff is arranged above the feed tray, the main column preferably has from 20 to 100 theoretical plates, in particular from 35 to 70 theoretical plates. Of these theoretical plates, the rectifying section generally accounts for from 5 to 30 theoretical plates, in particular from 10 to 20 theoretical plates, the middle section generally accounts for from 5 to 20 theoretical plates, in particular from 5 to 15 theoretical plates, and the stripping section generally accounts for from 10 to 50 theoretical plates, in particular from 20 to 35 theoretical plates.

The main column is preferably operated at a reflux ratio of from 5 to 80 kg/kg, in particular of from 10 to 50 kg/kg.

The side column usually has from 10 to 50 theoretical plates, in particular from 20 to 35 theoretical plates.

This column is preferably operated with a reflux ratio of from 1 to 20 kg/kg, in particular of from 2 to 10 kg/kg.

When the sidestream takeoff of the main column is arranged below the feed tray, the main column preferably has from 25 to 130 theoretical plates, in particular from 50 to 90 theoretical plates. Of these theoretical plates, the rectifying section generally accounts for from 5 to 30 theoretical plates, in particular from 10 to 20 theoretical plates, the middle section generally accounts for from 10 to 50 theoretical plates, in particular from 20 to 35 theoretical plates, and the stripping section generally accounts for from 10 to 50 theoretical plates, in particular from 20 to 35 theoretical plates.

In this arrangement, the main column is preferably operated with a reflux ratio of from 30 to 600 kg/kg, in particular of from 60 to 300 kg/kg.

The side column usually has from 5 to 20 theoretical plates, in particular from 5 to 15 theoretical plates. This column is preferably operated with an evaporation ratio of from 0.2 to 2.5 kg/kg, in particular of from 0.4 to 1.5 kg/kg.

The low boiler fraction removed contains up to 75% of MTBE. The remainder is substantially methanol. Furthermore, small amounts of water and also $C_4$-and $C_5$-hydrocarbons may also be present. This stream may be fed into the synthesis reactor of an MTBE plant. When only a small portion of the crude MTBE (fuel quality) from an MTBE plant is worked up to give highly pure MTBE, the low boiler fraction may be used as a fuel component.

It is possible to recycle the low and/or high boiler fraction into the fractional distillation, optionally while discharging a bleed stream.

Over 70% of the high boiler fraction, usually over 85%, consists of MTBE. It also comprises TBA, 2-methoxybutane, oligomers of butenes and their derivatives. This fraction may, optionally after hydrogenating the olefins contained therein, likewise be used as a fuel component.

The highly pure MTBE obtained by the process according to the invention has a purity of above 99.7%, preferably 99.8%, more preferably 99.9%. The hydrocarbon content is less than 0.1% by mass, preferably less than 0.02% by mass, the TBA content is less than 0.05% by mass, preferably less than 0.025% by mass, the methanol content is less than 0.02% by mass, preferably less than 0.01% by mass, and the water content is less than 200 ppm by mass, preferably less than 100 ppm by mass. Owing to its high purity, this MTBE may be used in the pharmaceuticals field, in analysis, as a solvent and as an extractant. It is particularly suitable as a solvent in organic syntheses, for example in the preparation of organometallic compounds and the reactions thereof. MTBE which furthermore has a 2-methoxybutane content of less than 500 ppm by mass is particularly well suited for the preparation of highly pure isobutene (by cleavage) to isobutene and methanol.

Such a process advantageously follows the process according to the invention for MTBE purification. A process for preparing highly pure isobutene by catalytically cleaving the MTBE having a purity of greater than 99.7% prepared according to any of claims 1 to 10 therefore also forms part of the subject matter of the present invention.

The examples which follow are intended to illustrate the invention without restricting its field of application which can be discerned from the description and the patent claims.

EXAMPLE 1

Removal of Low Boilers from Crude MTBE (Fuel Quality)

The distillative removal of the low boilers was carried out continuously in a first pilot plant column having a diameter of 50 mm. The column was filled with the Sulzer BX woven packing and had 25 theoretical plates.

The operating parameters were as follows:

| | |
|---|---|
| Feed rate | 14 kg/h |
| Distillate removal rate | 0.5 kg/h |
| Bottoms removal rate | 13.5 kg/h |
| Feed temperature | 80° C. |
| Top temperature | 80.8° C. |
| Bottom temperature | 93.5° C. |
| Top pressure | 3 bar |
| Feed tray | 8th theoretical plate from the bottom |
| Vapor loading factor | 0.75 $Pa^{0.5}$ |
| Liquid hourly space velocity | 10-20 $m^3/(m^2 * h)$ |
| Reflux ratio | 6 kg/kg |

The composition of column feed, distillate and bottom product was summarized in Table 1.

TABLE 1

Composition of the substance streams in column 1

| | Composition in % by mass | | |
|---|---|---|---|
| Substance | Column feed | Bottom product | Distillate |
| $C_4/C_5$-hydrocarbons | 0.299 | 0.02 | 8.477 |
| MTBE | 97.897 | 98.741 | 73.164 |
| 2-Methoxybutane | 0.299 | 0.309 | 0.017 |
| Methanol | 0.598 | 0.003 | 18.039 |
| tert-Butanol | 0.798 | 0.825 | 0.001 |
| Water | 0.010 | <0.001 | 0.302 |
| $C_8$-hydrocarbons | 0.100 | 0.103 | <0.001 |

Virtually water-and methanol-free MTBE was removed as the bottom product.

EXAMPLE 2

Removal of Highly Pure MTBE

Highly pure MTBE was continuously obtained by distillation from the bottom product of the first column in a second pilot plant column having a diameter of 50 mm. The column was filled with the Sulzer BX woven packing and had 50 theoretical plates.

The operating parameters were as follows:

| | |
|---|---|
| Feed rate | 2.5 kg/h |
| Distillate removal rate | 2.1 kg/h |
| Bottoms removal rate | 0.4 kg/h |
| Feed temperature | 94.7° C. |
| Top temperature | 71.7° C. |
| Bottom temperature | 74.0° C. |
| Top pressure | 1.7 bar |
| Feed tray | 24th theoretical plate from the bottom |
| Vapor loading factor | 0.75 Pa$^{0.5}$ |
| Liquid hourly space velocity | 10 m$^3$/(m$^2$ * h) |
| Reflux ratio | 6 kg/kg |

The composition of column feed, distillate and bottom product was summarized in Table 2.

TABLE 2

Composition of the substance streams in column 2

| | Composition in % by mass | | |
|---|---|---|---|
| Substance | Column feed | Bottom product | Distillate |
| C$_4$/C$_5$-hydrocarbons | 0.021 | <0.001 | 0.025 |
| MTBE | 98.739 | 92.040 | 99.922 |
| 2-Methoxybutane | 0.309 | 1.775 | 0.050 |
| Methanol | 0.003 | <0.001 | 0.004 |
| tert-Butanol | 0.825 | 5.500 | <0.001 |
| Water | <0.001 | <0.001 | <0.001 |
| C$_8$-hydrocarbons | 0.103 | 0.687 | <0.001 |

MTBE was obtained as a distillate in a purity of over 99.9%. Owing to its low content of protic accompanying materials (water, methanol, tert-butanol), this MTBE is in particular a good solvent for organometallic syntheses. Owing to the low 2-methoxybutane content, this MTBE is particularly suitable for the preparation of highly pure isobutene.

What is claimed is:

1. A process for preparing methyl tert-butyl ether having a purity of greater than 99.7% from technical grade methyl tert-butyl ether by fractional distillation, which comprises separating said technical grade methyl tert-butyl ether into a low boiler fraction comprising methyl tert-butyl ether, methanol and water, a middle fraction comprising methyl tert-butyl ether in a purity of greater than 99.7% and a high boiler fraction comprising tert-butyl alcohol and butene oligomers.

2. The process as claimed in claim 1, wherein the fractional distillation is carried out in at least two columns.

3. The process as claimed in claim 1, wherein the fractional distillation is carried out in at least one dividing wall column.

4. The process as claimed in claim 1, wherein the fractional distillation is carried out in a two-column system which consists of a main column and a side column, and the low boiler fraction is obtained as the top product and the high boiler fraction as the bottom product of the main column and the middle fraction is purified in the side column to give the methyl tert-butyl ether having a purity of greater than 99.7%.

5. The process as claimed in claim 4, wherein the methyl tert-butyl ether having a purity of greater than 99.7% is obtained as the top product of the side column.

6. The process as claimed in claim 4, wherein the methyl tert-butyl ether having a purity of greater than 99.7% is obtained as the bottom product of the side column.

7. The process as claimed in claim 4, wherein the fraction of the side column which does not comprise the methyl tert-butyl ether having a purity of greater than 99.7% is recycled into the main column.

8. The process as claimed in claim 1, wherein the methyl tert-butyl ether having a purity of greater than 99.7% has a 2-methoxybutane content of less than 500 ppm by mass.

9. The process as claimed in claim 1, wherein the low boiler fraction is recycled into the fractional distillation.

10. The process as claimed in claim 1, wherein the high boiler fraction is recycled into the fractional distillation.

11. A process for preparing highly pure isobutene by catalytically cleaving the methyl tert-butyl ether having a purity of greater than 99.7% prepared by the process as claimed in claim 1.

* * * * *